(12) United States Patent
Widberg et al.

(10) Patent No.: US 10,888,573 B2
(45) Date of Patent: Jan. 12, 2021

(54) PHOSPHOLIPID PREPARATIONS FOR THE IMPROVEMENT OF BRAIN PLASTICITY

(71) Applicant: ENZYMOTEC LTD., Migdal Ha'emeq (IL)

(72) Inventors: Asher Widberg, Haifa (IL); Hala Laoz, Kfar Kama (IL); Gai Ben-Dror, Gita (IL); Yifat Berkov, Kfar Saba (IL); Yael Lifshitz, Zichron Yaakov (IL); Yael Herzog, Gesher Haziv (IL)

(73) Assignee: ENZYMOTEC LTD., Migdal Haemeq (IL)

(*) Notice: Subject to any disclaimer, the term of this patent is extended or adjusted under 35 U.S.C. 154(b) by 0 days.

(21) Appl. No.: 16/082,468

(22) PCT Filed: Mar. 9, 2017

(86) PCT No.: PCT/IB2017/000281
§ 371 (c)(1),
(2) Date: Sep. 5, 2018

(87) PCT Pub. No.: WO2017/153841
PCT Pub. Date: Sep. 14, 2017

(65) Prior Publication Data
US 2019/0105336 A1    Apr. 11, 2019

Related U.S. Application Data

(60) Provisional application No. 62/306,329, filed on Mar. 10, 2016.

(51) Int. Cl.
*A61K 31/685*    (2006.01)
*A23D 9/013*    (2006.01)
(Continued)

(52) U.S. Cl.
CPC ............ *A61K 31/685* (2013.01); *A23D 9/013* (2013.01); *A23J 7/00* (2013.01); *A23K 20/158* (2016.05); *A23K 50/30* (2016.05); *A23K 50/60* (2016.05); *A23L 33/12* (2016.08); *A23L 33/40* (2016.08); *A61K 9/0029* (2013.01); *A61P 3/02* (2018.01);
(Continued)

(58) Field of Classification Search
CPC ......... A23D 9/013; A23J 7/00; A23K 20/158; A23K 50/30; A23K 50/60; A23L 33/12; A23L 33/40; A23V 2002/00; A61K 31/685; A61K 9/0029; A61P 25/28; A61P 3/02; C07F 9/106; C11B 11/00; C11C 3/04; Y02W 30/74
See application file for complete search history.

(56) References Cited

U.S. PATENT DOCUMENTS

2009/0074857 A1    3/2009    Dror et al.

FOREIGN PATENT DOCUMENTS

| WO | 2015/085192 A1 | 6/2015 |
| WO | 2016/016790 A1 | 2/2016 |

OTHER PUBLICATIONS

Lifshitz, Y. et al., "Sub-Chronic (13-week) Oral Toxicity Study, Preceded by an in Utero Exposure Phase and Genotoxicity Studies with Fish Source Phosphatidylserine in Rats"; Food and Chemical Toxicology (2015); vol. 86, pp. 234-244.
(Continued)

*Primary Examiner* — Savitha M Rao
(74) *Attorney, Agent, or Firm* — Fox Rothschild LLP

(57) ABSTRACT

Phospholipid preparations effective in improving brain development and brain rehabilitation are provided herein.

11 Claims, 5 Drawing Sheets

(51) Int. Cl.

| | | |
|---|---|---|
| *A23J 7/00* | (2006.01) | |
| *A23K 20/158* | (2016.01) | |
| *A23K 50/30* | (2016.01) | |
| *A23K 50/60* | (2016.01) | |
| *A23L 33/12* | (2016.01) | |
| *C11C 3/04* | (2006.01) | |
| *C11B 11/00* | (2006.01) | |
| *C11B 13/00* | (2006.01) | |
| *C07F 9/10* | (2006.01) | |
| *A23L 33/00* | (2016.01) | |
| *A61P 3/02* | (2006.01) | |
| *A61P 25/28* | (2006.01) | |
| *A61K 9/00* | (2006.01) | |

(52) U.S. Cl.
CPC .............. *A61P 25/28* (2018.01); *C07F 9/106* (2013.01); *C11B 11/00* (2013.01); *C11B 13/00* (2013.01); *C11C 3/04* (2013.01); *A23V 2002/00* (2013.01); *Y02W 30/74* (2015.05)

(56) References Cited

OTHER PUBLICATIONS

Hosokawa, M. et al., "Conversion to Docosahexaenoic Acid-Containing Phosphatidylserine from Squid Skin Lecithin by Phospholipase D-Mediated Transphosphatidylation"; J. Agric. Food Chem. (2000); vol. A8, pp. 4550-4554.

Extended European Search Report dated Sep. 11, 2019, issued in corresponding European Patent Application No. 17762599.3; 6 pgs.

PHOSPHOLIPID PREPARATIONS FOR THE IMPROVEMENT OF BRAIN PLASTICITY

FIELD OF THE INVENTION

The present invention relates to phospholipid preparations effective in improving brain development and brain rehabilitation.

BACKGROUND OF THE INVENTION

Neuronal plasticity refers to lasting change to the brain throughout the life course. It allows the central nervous system to develop properly and enables better brain rehabilitation and adaptation following brain injuries.

Structural and functional brain maturation are the underlying causes of developmental changes occurring during neurodevelopment in infants. It is a well-established fact that pre and post-natal experiences are fundamental for neurodevelopment. These include, but are not limited to, internal factors such as the transfer of materials from mother to infant or external sensorial events all responsible and contribute to normal cortical development. These prenatal and postnatal events are extremely important when considering preterm infants in which altered cerebral maturation is seen.

Development of the nervous system starts as early as gastrulation with several mechanisms such as genetic, epigenetic and environmental playing critical role in this process. Cerebral vesicles formation starts at the 5th week of gestation, followed by, neurogenesis and neuronal migration typically ending at 28th week of gestation. Other processes on the other hand, such as cortical differentiation and folding, can persist up to 3 years after birth. Other important events are myelination of white matter and neuronal connectivity which start at the third trimester and continues up to several years post-natal.

Although some of these processes are genetically controlled, it is now evident that nutrient intake is important aspect for normal fetal and postnatal development in term but also in preterm infants. Similarly, certain nutrient intake is an important aspect also for brain rehabilitation following brain injury. Consequences of nutrient deficiencies vary depending on the specific nutrient, timing, dosing and duration. Also important to note that consequences of nutrient insufficiency can last far beyond the period of dietary insufficiency. Of the most important nutrients for normal neurodevelopment in infants and children and for brain rehabilitation are lipids and phospholipids.

Glycerophospholipids, also referred to as phospholipids are key components of the lipid bilayer of cells, and are involved in cell metabolism and signaling. The hydroxyl groups of the glycerol backbone of phospholipids are substituted by a hydrophilic phosphate head and hydrophobic tail composed of non-polar fatty acids. Glycerophospholipids may be subdivided into distinct classes, based on the nature of the polar head group such as for example: phosphatidylcholine (also known as PC or lecithin), phosphatidylethanolamine (PE), and phosphatidylserine (PS). In addition to serving as a primary component of cellular membranes and binding sites for intracellular and intercellular proteins, some glycerophospholipids, such as phosphatidylinositols and phosphatidic acids are either precursors of, or are themselves, membrane-derived second messengers. Studies have shown that PS and PC enhance neuronal membrane function and improve memory skills. PS was found to have a beneficial effect in ADHD, depression, and chronic stress. In addition, PC was found to reduce emotional symptoms of premenstrual syndrome[1-3].

Multiple studies describe the importance of DHA and phospholipids and their mutual influence on brain and cognitive development. Early DHA supplementation support cognitive and visual development in infants at least partly mediated by phosphatidylserine accumulation as was shown in several studies.

Similarly, brain rehabilitation was shown to be affected by omega-3 fatty acids and phospholipids. Supplementation of lipids was shown not only to reduce neuronal damage but also exhibited rehabilitation and regeneration of the damaged brain. Lipids were shown to reduce neuro-inflammation and oxidative stress in addition to enhancing molecular pathways and elevating transcription factors mediating neuroprotection and ultimately survival of neuronal cells[4].

As we start to better understand the role of these compounds in cognitive development, we appreciate the importance of administrating these substances to infants, children and/or brain injured patients to support their brain maturation, plasticity and enable better brain development and rehabilitation. However, apparently, the origin of the phospholipids and their fatty acids (FA) content influence their activity. For example, the bio-functionality of soybean PS in the improvement of cognitive function has been shown to be different from that of other types of PS (see, WO 2005/037848). In addition, it was demonstrated that different ratios of specific fatty acids conjugated to PS can influence the efficacy of the PS in improving cognitive functions in elderly subjects with impaired cognitive performance (see, WO 2009/156991).

It is thus beneficial to apply the appropriate type of PS preparation for the specific indication.

SUMMARY OF THE INVENTION

The present invention provides a preparation comprising a non-mammalian derived mixture of phosphatidylserine wherein the percentage of linoleic acid (C18:2) attached to PS in the preparation with respect to the total fatty acid content attached to the PS in the preparation is lower than 8%, and the percentage of Docosahexaenoic acid (DHA) attached to PS in the preparation with respect to the total fatty acid content attached to the PS in the preparation is greater than 20%.

In one embodiment, the invention provides a preparation wherein the percentage of linoleic acid (C18:2) attached to PS in the preparation with respect to the total fatty acid content attached to the PS in the preparation is lower than 2.5%.

In one embodiment, the invention provides a preparation wherein the percentage of linoleic acid (C18:2) attached to PS in the preparation with respect to the total fatty acid content attached to the PS in the preparation is greater than 0.5%.

In one embodiment, the invention provides a preparation wherein at least 1% (w/w) of the PS in the preparation have a carbon number of 34 carbons.

In one embodiment, the invention provides a preparation wherein the at least 1% (w/w) of the PS in the preparation having carbon number of 34 carbons, have a double bond number of 1.

In one embodiment, the invention provides a preparation wherein the percentage of Docosahexaenoic acid (DHA) attached to PS in the preparation with respect to the total fatty acid content attached to the PS in the preparation is greater than 24%.

In one embodiment, the invention provides a preparation wherein the preparation comprises at least 1% (w/w) PS with fatty acid composition of 40 carbons.

In one embodiment, the invention provides a preparation wherein the at least 1% (w/w) of the PS in the preparation having a carbon number of 40 carbons, have a double bond number of 7.

In one embodiment, the invention provides a preparation wherein the phosphatidylserine constitutes at least 10% w/w of the preparation.

In one embodiment, the invention provides a preparation wherein the daily dose of the preparation provides 10-80 mg PS.

The present invention further provides a nutritional composition, pharmaceutical composition, nutraceutical composition, parenteral nutrition composition, functional food or medical food comprising any of the aforesaid preparations for use in enteral or parenteral preparations for administration to a subject.

The present invention further provides an infant formula, parenteral formula, baby food, toddler formula, child formula or adult formula comprising the preparation according to any one of the preceding claims for use in enteral or parenteral preparations for administration to a subject.

The present invention further provides any of the aforesaid preparations for use in a method for promoting development in a subject.

The present invention further provides any of the aforesaid preparations for use in a method for preventing and/or treating development delay in a subject.

The present invention further provides any of the aforesaid preparations for use in a method for preventing and/or treating development delay in preschoolers.

The present invention further provides any of the aforesaid preparations for use in a method for preventing and/or treating brain injuries (e.g. following a stroke or a traumatic brain injury).

In one embodiment, the invention provides any of the aforesaid preparations for use in a method for promoting brain and/or nervous system and/or cerebellar development in a subject.

In one embodiment, the invention provides any of the aforesaid preparations for use in a method for preventing and/or treating brain and/or nervous system and/or cerebellar development delay in a subject.

In one embodiment, the invention provides any of the aforesaid preparations for use in a method for promoting cognitive development in a subject.

In one embodiment, the invention provides any of the aforesaid preparations for use in a method for preventing and/or treating cognitive development delay in a subject.

In one embodiment, the invention provides any of the aforesaid preparations for use in a method for promoting visual and/or auditory development in a subject.

In one embodiment, the invention provides any of the aforesaid preparations for use in a method for preventing and/or treating visual and/or auditory development delays in a subject.

In one embodiment, the invention provides any of the aforesaid preparations for use in a method for promoting language and/or speech development in a subject.

In one embodiment, the invention provides any of the aforesaid preparations for use in a method for preventing and/or treating language and/or speech development delays in a subject.

In one embodiment, the invention provides any of the aforesaid preparations for use in a method for promoting social and/or emotional development in a subject.

In one embodiment, the invention provides any of the aforesaid preparations for use in a method for preventing and/or treating social and/or emotional development delays in a subject.

In one embodiment, the invention provides any of the aforesaid preparations for use in a method for promoting motor development in a subject.

In one embodiment, the invention provides any of the aforesaid preparations for use in a method for preventing and/or treating motor development delays in a subject.

In one embodiment, the invention provides any of the aforesaid preparations for use in a method for increasing brain weight in a subject.

In one embodiment, the invention provides any of the aforesaid preparations for use in a method for increasing the number and/or the density of granule cells in a subject.

In one embodiment, the invention provides any of the aforesaid preparations for use in a method for improving electrochemical synapse signaling.

In one embodiment, the invention provides any of the aforesaid preparations for use in a method for increasing neurogenesis in a subject.

In one embodiment, the invention provides any of the aforesaid preparations for use in a method for increasing survival in a subject.

In one embodiment, the invention provides any of the aforesaid uses wherein said subject is an infant, a child a preschooler, an adolescence or an adult.

In one embodiment, the invention provides any of the aforesaid uses, wherein said subject is an infant.

In one embodiment, the invention provides any of the aforesaid uses, wherein said infant is a preterm infant.

In one embodiment, the invention provides any of the aforesaid uses, wherein said subject is a healthy subject or a non-healthy subject.

In one embodiment, the invention provides any of the aforesaid uses, wherein said subject is any one of a subject being under parenteral nutrition, a subject being under partial parenteral nutrition, a subject that cannot tolerate enteral feeding or a subject that requires non enteral feeding.

In one embodiment, the invention provides any of the aforesaid uses, wherein said subject is under parenteral nutrition.

The present invention further provides a method of promoting development in a subject in need thereof, comprising administering to the subject in need thereof any of the aforesaid preparations or compositions.

In one embodiment, the present invention further provides a method of preventing and/or treating development delay in a subject (e.g. a preschooler child), comprising administering to the subject in need thereof any of the aforesaid preparations or compositions.

In one embodiment, the present invention further provides a method of preventing and/or treating brain injuries in a subject (e.g. a subject following a stroke or traumatic brain injury), comprising administering to the subject in need thereof any of the aforesaid preparations or compositions.

In one embodiment, the present invention further provides a method of promoting brain and/or nervous system and/or cerebellar development in a subject, comprising administering to the subject in need thereof any of the aforesaid preparations or compositions.

In one embodiment, the present invention further provides a method of preventing and/or treating brain and/or nervous system and/or cerebellar development delay in a subject, comprising administering to the subject in need thereof any of the aforesaid preparations or compositions.

In one embodiment, the present invention further provides a method of promoting cognitive development in a subject, comprising administering to the subject in need thereof any of the aforesaid preparations or compositions.

In one embodiment, the present invention further provides a method of preventing and/or treating cognitive development delay in a subject, comprising administering to the subject in need thereof any of the aforesaid preparations or compositions.

In one embodiment, the present invention further provides a method of promoting visual and/or auditory development in a subject, comprising administering to the subject in need thereof any of the aforesaid preparations or compositions.

In one embodiment, the present invention further provides a method of preventing and/or treating visual and/or auditory development delays in a subject, comprising administering to the subject in need thereof any of the aforesaid preparations or compositions.

In one embodiment, the present invention further provides a method of promoting language and/or speech development in a subject, comprising administering to the subject in need thereof any of the aforesaid preparations or compositions.

In one embodiment, the present invention further provides a method of preventing and/or treating language and/or speech development delays in a subject, comprising administering to the subject in need thereof any of the aforesaid preparations or compositions.

In one embodiment, the present invention further provides a method of promoting social and/or emotional development in a subject, comprising administering to the subject in need thereof any of the aforesaid preparations or compositions.

In one embodiment, the present invention further provides a method of preventing and/or treating social and/or emotional development delays in a subject, comprising administering to the subject in need thereof any of the aforesaid preparations or compositions.

In one embodiment, the present invention further provides a method of promoting motor development in a subject, comprising administering to the subject in need thereof any of the aforesaid preparations or compositions.

In one embodiment, the present invention further provides a method of preventing and/or treating motor development delays in a subject, comprising administering to the subject in need thereof any of the aforesaid preparations or compositions.

In one embodiment, the present invention further provides a method of increasing brain weight in a subject, comprising administering to the subject in need thereof any of the aforesaid preparations or compositions.

In one embodiment, the present invention further provides a method of increasing the number and/or density of granule cells in a subject, comprising administering to the subject in need thereof any of the aforesaid preparations or compositions.

In one embodiment, the present invention further provides a method of improving electrochemical synapse signaling in a subject, comprising administering to the subject in need thereof any of the aforesaid preparations or compositions.

In one embodiment, the present invention further provides a method of increasing neurogenesis in a subject, comprising administering to the subject in need thereof any of the aforesaid preparations or compositions.

In one embodiment, the present invention further provides a method increasing survival in a subject, comprising administering to the subject in need thereof any of the aforesaid preparations or compositions.

The present invention further provides a pharmaceutical or nutritional composition, comprising a non-mammalian derived mixture of phosphatidylserine (PS), wherein the percentage of linoleic acid (C18:2) attached to PS in the preparation with respect to the total fatty acid content attached to the PS in the preparation is 0.7%, wherein the percentage of Docosahexaenoic acid (DHA) attached to PS in the preparation with respect to the total fatty acid content attached to the PS in the preparation is 25%, wherein at least 1% (w/w) of the PS in the preparation have a carbon number of 34 carbons, further comprising one or more pharmaceutically or nutritionally acceptable excipients or carriers.

The present invention further provides a method of treating a subject in need for the treatment with any of the aforesaid preparations or compositions, wherein a daily dose of the preparation or composition provides 10-80 mg PS to the subject.

DETAILED DESCRIPTION OF THE INVENTION

Figure 1:
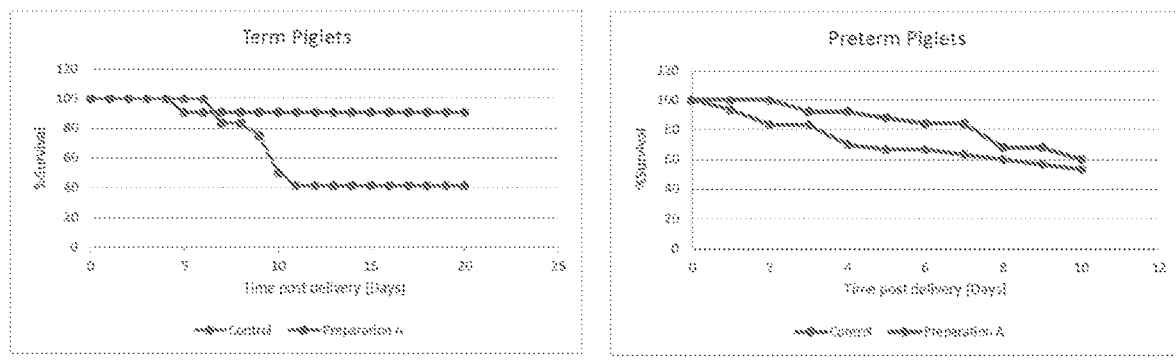
FIG. 1 illustrates Survival curves for piglets fed with preparation A (red curve) or control (Diet C, blue curve). A) Piglets delivered at term and fed with preparation A (n=13) or C (n=12) for 20 days. B) Preterm piglets fed with preparation A (n=20) or C (n=25) for 10 days.
Figure 2:
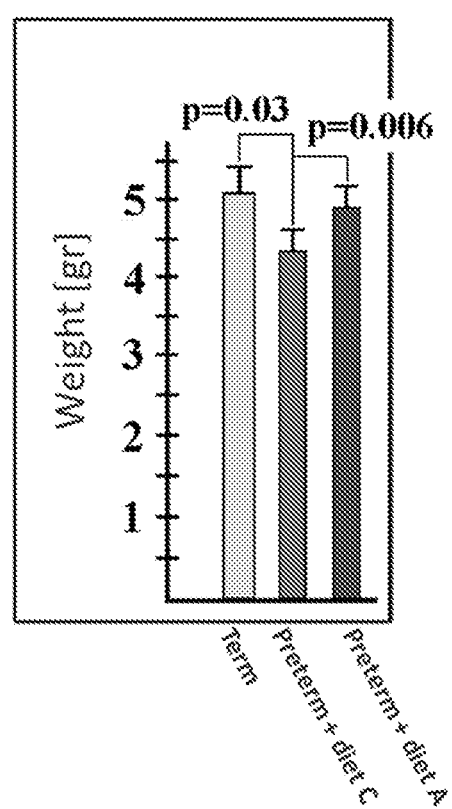
FIG. 2 shows the cerebellar weight of term pigs (euthanized at day 0 post-delivery to serve as a control for preterm piglets grown for 10 days, n=4, green column), preterm pigs fed with preparation C (n=7, red column), and preterm pigs fed with preparation A (n=10, blue column).

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is lower than 8%, and the percentage of Docosahexaenoic acid (DHA) attached to PS in the preparation with respect to the total fatty acid content attached to the PS in the preparation is greater than 20%.

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is lower than 8%, and the percentage of Docosahexaenoic acid (DHA) attached to PS in the preparation with respect to the total fatty acid content attached to the PS in the preparation is greater than 20% and wherein at least 1% (w/w) of the PS in the preparation have a carbon number of 34 carbons.

In one of its aspects the present invention provides a preparation comprising non-mammalian derived mixture of phosphatidylserine wherein the percentage of linoleic acid (C18:2) attached to PS in the preparation with respect to the total fatty acid content attached to the PS in the preparation is lower than 2.5%, and the percentage of Docosahexaenoic acid (DHA) attached to PS in the preparation with respect to the total fatty acid content attached to the PS in the preparation is greater than 20%.

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is lower than 2.5%, and the percentage of Docosahexaenoic acid (DHA) attached to PS in the preparation with respect to the total fatty acid content attached to the PS in the preparation is greater than 20% and wherein at least 1% (w/w) of the PS in the preparation have a carbon number of 34 carbons.

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is greater than 0.05% and lower than 2.5%, and the percentage of Docosahexaenoic acid (DHA) attached to PS in the preparation with respect to the total fatty acid content attached to the PS in the preparation is greater than 20%.

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is greater than 0.05% and lower than 2.5%, and the percentage of Docosahexaenoic acid (DHA) attached to PS in the preparation with respect to the total fatty acid content attached to the PS in the preparation is greater than 20% and wherein at least 1% (w/w) of the PS in the preparation have a carbon number of 34 carbons.

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is greater than 0.5% and lower than 2.5%, and the percentage of Docosahexaenoic acid (DHA) attached to PS in the preparation with respect to the total fatty acid content attached to the PS in the preparation is greater than 20%.

In one of its aspects the present invention provides a preparation comprising a non-mammalian derived mixture of phosphatidylserine wherein the percentage of linoleic acid (C18:2) attached to PS in the preparation with respect to the total fatty acid content attached to the PS in the preparation is greater than 0.5% and lower than 2.5%, and the percentage of Docosahexaenoic acid (DHA) attached to PS in the preparation with respect to the total fatty acid content attached to the PS in the preparation is greater than 20% and wherein at least 1% (w/w) of the PS in the preparation have a carbon number of 34 carbons.

The terms "glycerophospholipid" and "phospholipids" are used herein interchangeably and should be understood to encompass a lipid of the general formula:

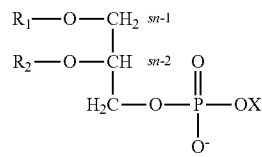

wherein X represents a moiety selected from serine, choline, ethanolamine, inositol, glycerol and hydrogen, and R1 and R2, which may be identical or different, independently represent hydrogen or an acyl group, wherein the acyl group is selected from saturated, mono-unsaturated or poly-unsaturated acyl groups (PUFA). The sn-1 and sn-2 positions as used herein and as indicated in above formula, refer to the respective carbon atoms on the glycerol backbone wherein R1 and R2, are hydrogen or acyl groups substituted on the corresponding position. When X is serine, i.e. —CH2CH(COOH)NH2, the phospholipid is referred to as serine glycerophospholipid or phosphatidylserine (PS).

As described herein, the terms "substituted," "conjugated,", and "attached" are used interchangeably and should be understood to encompass a fatty acid acyl covalently attached to the glycerophospholipid backbone of a phospholipid of the invention. As noted above, the fatty acid may be attached to the sn-1 and/or sn-2 positions.

As used herein, the term "fatty acid" should be understood to encompass a carboxylic acid with a unbranched aliphatic tail (chain), which is either saturated, or unsaturated having one unsaturated bond (mono-unsaturated fatty acids) or two or more unsaturated bonds (poly-unsaturated fatty acids). When referring to a "fatty acid acyl" it should be understood to encompass an —C(=O)—R radical wherein R is a long unbranched aliphatic tail, which is either saturated or unsaturated having one unsaturated bond (mono-unsaturated fatty acids) or two or more unsaturated bonds (poly-unsaturated fatty acids).

As used herein, the term ω-X, Omega-X, n-X (X denotes a number), are interchangeably used and should be understood to denote the carbon atom furthest from the carboxyl group of a fatty acid.

Non-limiting examples of saturated fatty acids include: Butyric acid (Butanoic acid, C4:0), Caproic acid (Hexanoic acid, C6:0), Caprylic acid (Octanoic acid, C8:0), Capric acid (Decanoic acid, C10:0), Lauric acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids include: Myristoleic acid (C14:1, ω-5), Palmitoleic acid (C16:1, ω-7), Oleic acid (C18:1, ω-9), Linoleic acid (C18:2, ω-6), Linolenic acid (C18:3) [Alpha-linolenic acid (C18:3, ω-3), Gamma-linolenic acid (C18:3, ω-6)], Eicosenoic acid (C20:1, ω-9), Arachidonic acid (C20:4, ω-6), Eicosapentaenoic acid (C20:5, ω-3), Erucic acid (C22:1, ω-9), Docosapentanoic acid (C22:5, ω-3) and Docosahexaenoic acid (C22:6, ω-3), Nervonic acid (C24:1, ω-9).

The term phosphatidylserine is often also referred to in the literature as serine glycerophospholipid, phosphatidyl serine, and PS.

As used herein, the term "carbon number" should be understood to encompass the sum of carbon atoms present on both fatty acids (R1 and R2) attached to one molecule of phospholipid (e.g. phosphatidylserine).

As used herein, the term "double bond number" should be understood to encompass the sum of double bonds present on both fatty acids (R1 and R2) attached to one molecule of phospholipid (e.g. phosphatidylserine).

In some embodiments, a preparation according to the invention comprises a non-mammalian derived mixture of phosphatidylserine wherein the percentage of linoleic acid (C18:2) attached to PS in the preparation with respect to the total fatty acid content attached to the PS in the preparation is lower than 8%, at times lower than 6%, at times lower than 4%, at times less than 3%, at times less than 2.5% and at times less than 1%. In some embodiments, a preparation according to the invention comprises a non-mammalian derived mixture of phosphatidylserine wherein the percentage of linoleic acid (C18:2) attached to PS in the preparation with respect to the total fatty acid content attached to the PS in the preparation is greater than 0.05% and lower than 8%, at times greater than 0.05% and lower than 5%, at times greater than 0.05% and lower than 4%, at times greater than 0.05% and lower than 2.5%, at times greater than 0.1% and lower than 2.5%, at times greater than 0.5% and lower than 2.5%, at times greater than 0.5 and lower than 1.5%, at times greater than 0.1% and lower than 1% and at times greater than 1% and lower than 1.5%.

In some embodiments, a preparation according to the invention comprises a non-mammalian derived mixture of phosphatidylserine wherein the percentage of Docosahexaenoic acid (DHA) attached to PS in the preparation with respect to the total fatty acid content attached to the PS in the preparation is greater than 20%, at times greater than 22%, at times greater than 24%, at times greater than 25%, at times greater than 28%, at times greater than 30% and at times greater than 35%. In some embodiments, a preparation according to the invention comprises a non-mammalian derived mixture of phosphatidylserine wherein the percentage of Docosahexaenoic acid (DHA) attached to PS in the preparation with respect to the total fatty acid content attached to the PS in the preparation is greater than 22% and lower than 50%, at times greater than 23% and lower than 45%, at times greater than 24% and lower than 45%, at times greater than 22% and lower than 30%, at times greater than 23% and lower than 30%, at times greater than 24% and lower than 30%, at times greater than 28% and lower than 45%, at times greater than 30% and lower than 45%, at times greater than 35% and lower than 45%, and at times greater than 25% and lower than 30%.

In some embodiments at least 1% (w/w) of the PS in a preparation according to the invention have a carbon number of 34 carbons. In some embodiments at least 2% (w/w), at times at least 3% (w/w), at times at least 5% (w/w), at times at least 8% (w/w) and at times at least about 10% (w/w) of the PS in a preparation according to the invention have a carbon number of 34 carbons. In some embodiments at least 1% (w/w) and less than 22% (w/w), at times at least 2% (w/w) and less than 20% (w/w), at times at least 3% (w/w) and less than 10% (w/w) and at times at least 4% (w/w) and less than 8% (w/w) of the PS in a preparation according to the invention have a carbon number of 34 carbons.

According to some embodiments PS with a carbon number of 34 carbons contains a double bond number of 1.

In some embodiments at least 1% (w/w) of the PS in a preparation according to the invention have a carbon number of 36 carbons. In some embodiments at least 2% (w/w), at times at least 3% (w/w), at times at least 5% (w/w), at times at least 8% (w/w), at times at least about 10% (w/w), at times at least 15% (w/w) and at times at least 20% (w/w) of the PS in a preparation according to the invention have a carbon number of 36 carbons. In some embodiments at least 1% (w/w) and less than 30% (w/w), at least 1% (w/w) and less than 20% (w/w), at times at least 1% (w/w) and less than 10% (w/w), at times at least 2% (w/w) and less than 30% (w/w), at times at least 3% (w/w) and less than 20% (w/w) of the PS in a preparation according to the invention have a carbon number of 36 carbons.

In some embodiments at least 1% (w/w) of the PS in a preparation according to the invention have a carbon number of 38 carbons. In some embodiments at least 2% (w/w), at times at least 3% (w/w), at times at least 5% (w/w), at times at least 8% (w/w), at times at least about 10% (w/w), at times at least 15% (w/w), at times at least 20% (w/w), at times at least 30% (w/w) and at times at least 40% (w/w) of the PS in a preparation according to the invention have a carbon number of 38 carbons. In some embodiments at least 1% (w/w) and less than 60% (w/w), at times at least 5% (w/w) and less than 50% (w/w), at times at least 5% (w/w) and less than 40% (w/w), at times at least 10% (w/w) and less than 50% (w/w) of the PS in a preparation according to the invention have a carbon number of 38 carbons.

In some embodiments at least 1% (w/w) of the PS in a preparation according to the invention have a carbon number of 40 carbons. In some embodiments at least 2% (w/w), at times at least 3% (w/w), at times at least 5% (w/w), at times at least 8% (w/w), at times at least about 10% (w/w), at times at least 15% (w/w) and at times at least 20% (w/w) of the PS in a preparation according to the invention have a carbon number of 40 carbons. In some embodiments at least 1% (w/w) and less than 20% (w/w), at times at least 1% (w/w) and less than 10% (w/w), at times at least 2% (w/w) and less than 8% (w/w), at times at least 3% (w/w) and less than 6% (w/w) of the PS in a preparation according to the invention have a carbon number of 40 carbons.

According to some embodiments the PS in the preparation of the invention has a double bond number of 7, at times 6, at times 5, at times 4, at times 3, at times 2 and at times 1.

In some embodiments, a preparation according to the invention comprises a concentration of phosphatidylserine of at least 10% w/w, at times at least 20% w/w, at times at least 40% w/w, at times at least 50% w/w, at times at least 60% w/w and at times at least 70% w/w. In some embodiments, a preparation according to the invention comprises a concentration of phosphatidylserine of between 20% w/w to 80% w/w, at times between 20% w/w to 70% w/w, at times between 20% w/w to 60% w/w, at times between 30% w/w to 80% w/w, at times between 30% w/w to 70% w/w, at times between 30% w/w to 60% w/w, at times between 40% w/w to 80% w/w, at times between 40% w/w to 70% w/w, at times between 40% w/w to 60% w/w, at times between 30% to 100%, at times between 50% to 100%, at tiems between 50% to 80%, at times between 60% to 100%, at times between 70% to 100%, at times between 80% to 100%, at times between 70% to 90% and at times between 90% to 100%.

It should be noted that the preparation of the invention may also comprise other phospholipids, such as phosphatidylcholine (PC), phosphatidylethanolamine (PE), phosphatidylinositol (PI), phosphatidylglycerol (PG) and phosphatidic acid (PA), to which fatty acid acyls are covalently attached (bonded) at either or both of the sn-1 or sn-2 positions of the glycerol moiety of the phospholipid.

According to some embodiments the ratio in a preparation according to the invention between: the percentage of linoleic acid (C18:2) attached to PS in the preparation with respect to the total fatty acid content attached to the PS in the preparation, to the: percentage of Docosahexaenoic acid (DHA) attached to PS in the preparation with respect to the total fatty acid content attached to the PS in the preparation is below 0.09, at times below 0.07, at times below 0.05, at times below 0.04, at times below 0.03, at times below 0.02, at times below 0.01. According to some embodiments the ratio between: the percentage of linoleic acid (C18:2) attached to PS in the preparation with respect to the total fatty acid content attached to the PS in the preparation, to the: percentage of Docosahexaenoic acid (DHA) attached to PS in the preparation with respect to the total fatty acid content attached to the PS in the preparation is between 0.001 to 0.07, at times between 0.001 to 0.05, at times between 0.01 to 0.07, at times between 0.02 to 0.06, and at times between 0.03 to 0.05.

According to some embodiments the ratio in a preparation according to the invention between: the percentage of linoleic acid (C18:2) attached to PS in the preparation with respect to the total fatty acid content attached to the PS in the preparation, to the: percentage of Eicosapentaenoic acid (EPA) attached to PS in the preparation with respect to the total fatty acid content attached to the PS in the preparation is below 0.5, at times below 0.4, at times below 0.3 at times below 0.2, at times below 0.15, at times below 0.1, at times below 0.05, at times below 0.03, at times below 0.02, at times below 0.01. According to some embodiments the ratio between: the percentage of linoleic acid (C18:2) attached to PS in the preparation with respect to the total fatty acid content attached to the PS in the preparation, to the: percentage of Eicosapentaenoic acid (EPA) attached to PS in the preparation with respect to the total fatty acid content attached to the PS in the preparation is between 0.02 to 1, at times between 0.02 to 0.8, at times between 0.02 to 0.6, at times between 0.02 to 0.5, at times between 0.02 to 0.4, at times between 0.02 to 0.3 at times between 0.02 to 0.2, at times between 0.03 to 0.2 and at times between 0.05 to 0.1.

According to some embodiments the ratio in a preparation according to the invention between: the percentage of linolenic acid (C18:3) attached to PS in the preparation with respect to the total fatty acid content attached to the PS in the preparation, to the: percentage of Docosahexaenoic acid (DHA) attached to PS in the preparation with respect to the total fatty acid content attached to the PS in the preparation is below 0.1, at times below 0.05, at times below 0.03 and at times below 0.01.

According to some embodiments the ratio in a preparation according to the invention between: the percentage of linolenic acid (C18:3) attached to PS in the preparation with respect to the total fatty acid content attached to the PS in the preparation, to the: percentage of Eicosapentaenoic acid (EPA) attached to PS in the preparation with respect to the total fatty acid content attached to the PS in the preparation is below 0.05, at times below 0.04, at times below 0.03, at times below 0.02, at times below 0.01.

According to some embodiments a preparation according to the invention contains a ratio between fatty acids that are attached to PS in the preparation with respect to the total fatty acid content attached to the PS in the preparation that is such that the percentage of DHA is greater than the percentage of EPA, the percentage of EPA is greater than the percentage of linoleic acid (18:2), and optionally, the percentage of linoleic acid (18:2) is greater or equal the percentage of linolenic acid (18:3).

According to some embodiments the fatty acids profile of the fatty acids attached to the PS in a preparation according to the invention corresponds to the fatty acid profile of fish.

Quantification of Phospholipids by 31P-NMR Spectroscopy Using the Internal Standard Method.

Purpose: This method is used to determine the phospholipid content by weight in the preparation.

Instruments: Bruker Avance III 600 MHz with automatic sample changer and cQNP probe head. Bruker Avance 300 MHz with automatic sample changer and BBI probe head. For the quantification of phospholipids in the preparation of the invention (powder form) approximately 300 mg of the test substance and 20 mg of internal standard TPP (triphenylphosphate) is dissolved in 1.5 ml CDCl3, 3 ml methanol and 3 ml aqueous Cs-EDTA solution (0.2 m, pH 7.5). After 15 minutes of shaking, the organic layer is separated by centrifugation and measured with 31P-NMR. The integrated signals of the test substance and of the internal standard TPP (triphenylphosphate) are used for calculation. The ratio of integrals corresponds to the molar ratio of the compared substances. For calculation software Microsoft Excel 14.0 is used.

Calculation:

$$MOL_{IS}[\text{mMol}] = \frac{W_{IS}[\text{mg}] * C_{IS}[\%]}{MW_{IS}[\text{g/Mol}] * 100} \qquad \text{Equation 1}$$

$$MOL_P[\text{mMol}] = \frac{I_P * H_{IS} * MOL_{IS}[\text{mMol}]}{I_{IS} * H_P} \qquad \text{Equation 2}$$

$$\text{weight-}\%_P = \frac{MW_P[\text{g/Mol}] * MOL_P[\text{mMol}] * 100}{W_P[\text{mg}]} \qquad \text{Equation 3}$$

Declaration of Variables:

|  | test substance | internal standard |
|---|---|---|
| molecular weight | $MW_P$ (According to the MW table presented below) | $MW_{IS}$ |
| initial weight [mg] | $W_P$ | $W_{IS}$ |
| content [%-by weight] | weight-$\%_P$ | $C_{IS}$ |
| Mol [mMol] | $MOL_P$ | $MOL_{IS}$ |
| integral | $I_P$ | $I_{IS}$ |
| number of P-atoms | $H_P$ | $H_{IS}$ |

| Phospholipid | $MW_P$ (g/mol) |
|---|---|
| Phosphatidylcholine (PC) | 812.0 |
| Lyso Phosphatidylcholine (LPC) | 534.5 |
| Phosphatidylinositol (PI) | 907.0 |
| Lyso Phosphatidylinositol (LPI) | 629.5 |
| Phosphatidylserine (PS) | 833.0 |
| Lyso Phosphatidylserine (LPS) | 555.5 |
| Phosphatidyl Ethanolamine (PE) | 770.0 |
| Lyso Phosphatidyl Ethanolamine (LPE) | 492.5 |
| Phosphatidic Acid (PA) | 746.0 |
| Lyso Phosphatidic Acid (LPA) | 468.5 |
| Acyl Phosphatidyl Ethanolamine (APE) | 1032.0 |
| Other | 812.0 |

Determination of Fatty Acid Percentage in Phospholipids

Purpose: This method is used to determine the percentage of a fatty acid (e.g., Docosahexaenoic acid (DHA) or linoleic acid (C18:2)) attached to the PS in the preparation out of the total fatty acid content attached to the PS in the preparation.

Materials: Acetic acid glacial A.R., Methanol abs. A.R., Chloroform A.R., Acetone A.R., Hexane A.R., Toluene A.R., Di-isopropyl ether AR., Butylhydroxytoluene, Sigma Lot #W218405 or equivalent, Sodium Sulfate Anhydrous, Sigma, Lot #31481, or equivalent, Sodium methoxide 25% (w/w) in methanol, Sigma Cat #15625-6, or equivalent, Primuline, Sigma Cat #206865, or equivalent, GC reference standard, Nuchek Lot #566B, Phosphatidylcholine reference standard, Sigma Aldrich Lot Cat #P3556, or equivalent, Phosphatidylserine reference standard, Sigma Aldrich Lot Cat #P5660, or equivalent, TLC Plates 20×10, silica gel 60 F254 layer MERCK 1.05715, or equivalent.

Apparatus: Orbital shaker with temperature control, Analytical Balance, Pipettor 0.2-1 ml and 1-5 ml range, Volumetric pipette 10 ml class A, TLC tank, suitable for 20×10 TLC plates, Disposable capillaries 5 µl volume, GC systems suitable for use with capillary column, equipped with oven capable of maintaining temperature with +0.1 C degree accuracy, FID detector, split mode injection unit with temperature controller, GC capillary column, G16 USP phase, length 30 m, I.D. 0.25 mm, film 0.25 µm, or similar.

Reagents and Solutions Preparation:

Sodium Methoxide solution: Accurately weigh 54 g of Sodium methoxide 25% into a 500 ml volumetric flask. Dilute to volume with Methanol Abs. Store in a dark place, in a tightly closed glass container. Solution is stable for up to 3 months.

Chloroform:Methanol 95:5 solution: Mix 95 volumes of Chloroform with 5 volumes of Methanol. Store in a dark place, in a tightly closed glass container. Solution is stable for up to one year.

Developing solution: Mix Water, Methanol, Acetic acid, Acetone and Chloroform in a volume ratio of 5:10:15:20:50, respectively. Store in a dark place, in a tightly closed glass container. Solution is stable for up to one year.

Primuline solution: Weight 10 mg into a 100 ml volumetric flask. Add 60 ml Acetone and 40 ml water. Mix well. Store in a dark place, in a tightly closed glass container. Solution is stable for up to one year.

Antioxidant solution 1 mg/ml: Weighed 25±2 mg Butylhydroxytoluene into a 25 ml volumetric flask. Add Toluene to the Mark, mix well (This solution can be kept for 3 month at room temperature.).

Antioxidant solution 0.05 mg/ml: Pipette 10 ml of the above solution into a 200 ml volumetric flask, add Toluene to the Mark, mix well. Store at 50° C. for up to 3 months. (This solution can be kept for 3 months at room temperature).

PS/PC mix standard solution: Add about 20 mg of Phosphatidylserine reference standard into a 2 ml volumetric flask, add about 20 mg of Phosphatidylcholine reference standard. Add a small amount of Chloroform:Methanol solution sufficient to dissolve the reference standards. Once dissolved fill up to volume with the same Chloroform:Methanol solution. Store in a tightly closed container at −20° C. Stable for up to 3 months.

System suitability solution: Empty an ampoule containing 100 mg of GC reference standard 566B into a 50 ml volumetric flask, add 0.05 mg/ml Antioxidant Solution to the Mark. Mix well. Store in tightly closed container at −20° C. Stable for up to 3 months.

Procedure:

Sample solution preparation: Accurately weight 500 mg of the sample into a 20 ml vial with ground stopper. Add 10 ml Chloroform: Methanol solution and shake vigorously for 2-3 minutes.

Phospholipids purification: Perform test in duplicate. Perform blank determination by developing an unloaded plate (no sample applied to the plate). Sample silica from an area corresponding to the area of the sample followed by methylation as described above. Apply an even thin band of 120 µl sample solution on TLC plate, 1 cm above the plate bottom, leaving a 3 cm margin on each side. At one of the margins, apply PS/PC mix standard solution of approximately 5 µl, spot wise by means of a disposable capillary. Add 45 ml of di-isopropyl ether to the 20×10 mm Glass TLC chamber. Saturate the chamber for 15-20 minutes. Develop TLC plate up to about 90 mm mark. Dry the plate in fume hood under air at room temperature for about 10 minutes. Repeat the previous two steps once more using the same chamber. Add 45 ml of developing solution to the 20×10 mm Glass TLC chamber. Saturate the chamber for 15-20 minutes. Develop TLC plate up to about 80 mm mark. Dry the plate in fume hood under a current of air at room temperature for about 10 minutes. Spray the TLC plate evenly with Primuline solution and dry under a current of air at room temperature for about 10 minutes. Place the plate under UV lamp at 365 nm to observe the bands. Identify the corresponding bands using spots of PS mix reference standard and scrub the bands in-to a 20 ml glass vial with ground stopper.

Methylation: To the 20 ml vials containing scrubbed silica add 2 ml Toluene. Then add 4 ml of Sodium methoxide solution. Shake for 15 minutes at 50° C. Then add 200 µl of Acetic acid and 4 ml of purified water, shake vigorously for 1 minute. Add 2 ml of Hexane and shake vigorously for 30 seconds. Transfer only the upper organic layer to a 20 ml bottle. Again add 2 ml of Hexane and shake vigorously for 30 seconds. Transfer only the upper organic layer to the same 20 ml bottle. Combine organic phases and dry over 0.5 grams Sodium sulfate. Filter through a 0.2 micron filter. Evaporate hexane under a nitrogen stream, until a volume of about 0.5 ml is reached. Analyze the sample by Gas Chromatography.

Gas Chromatography Settings:

| Column | Capillary column, G16 USP phase, length 30 m, I.D. 0.25 mm, film 0.25 µm, or similar |
| --- | --- |
| Carrier gas | Helium |
| Equilibration time | 2 min |

| Temperatures | Initial Temp | Initial Time | First Temp. rate | Final Temp. | Hold Time |
| --- | --- | --- | --- | --- | --- |
| | 170° C. | 2 min | 1° C./min | 210° C. | 2 min |
| | | | Second Temp. rate | Final Temp. | Hold Time |
| | | | 30° C./min | 240° C. | 11 min |

| Injector temp. | 250° C. |
| --- | --- |
| Pressure | 21 psi |
| Split ratio | 25:1 |
| Helium flow | 1.5 ml/min (constant flow) |
| Total flow | 41.4 ml/min |
| Detector temp. | 270° C. |
| Hydrogen flow | 40 ml/min |
| Air flow | 400 ml/min |
| Injection volume | 1 µl |

Note:
Gas flow and temperature ramp may be adjusted to meet system suitability acceptance criteria.

Chromatography Injection Order: First inject Hexane and insure that there is no response in the relevant retention time. Next, inject System Suitability solution. The acceptance criteria is as follows: the resolution (R) between the peaks due to methyl oleate (C18:1n9) and methyl cis-vaccinate (C:181n11)≥1.3.

$$\text{resolution } R = \frac{2(t2 - t1)}{1.7(W1 + W2)}$$

where, t1 and t2 are the retention times of the two components and W1 and W2 are the corresponding widths at half-height of the peaks.

Next, inject sample from blank TLC plate (TLC blank). If there are peaks observed in the TLC blank chromatogram (except the solvent peak), they must be subtracted from the chromatogram of the sample. Finally, inject Samples.

Calculation: Calculate the area percentage of a fatty acid component in sample by the formula: % FA=AreaFA/AreaTot, where AreaFA is the area of the peak response obtained for an individual fatty acid methyl ester and AreaTot is the sum of the peak areas of all of the peaks, corresponding to fatty acids methyl esters. Report the results indicating two digits after decimal point. Relative standard deviation between the replicates should not exceed 5%.

The following Example is a representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

A preparation as described herein may be optionally prepared through enzymatic, chemical or molecular biology methods. Briefly, a phospholipid mixture can be enriched with the required fatty acids (e.g. EPA, Palmitic acid, DHA, oleic acid, linoleic acid) by enzymatic processes, e.g. enrichment of a natural phospholipid with specific fatty acids by enzymatic transesterification/esterification. Another pathway to acquire the preparation is to obtain a phospholipid source which is naturally rich in the required fatty acids, such as marine-derived lecithin (e.g. krill, fish, algae, and squid) or eggs phospholipids. Usually, In order to obtain the requested ratio between the different phospholipids in the mixture transformation of the phospholipid head group to serine (using PLD enzymes) is required to obtain PS. Such methods have been described in WO 2005/038037. Alternatively, the phospholipid mixture, according to at least some embodiments of the present invention can be prepared by GMO (genetically modified organisms)/biotechnology methods, for example, providing phospholipids-producing organisms with the required fatty acids to obtain the different phospholipids conjugates.

According to another embodiment of the present invention, the preparation is preferably prepared from a natural, synthetic or semi-synthetic source or any combinations thereof. In an embodiment of the present invention, the natural source is derived from any one of plant (such as for example soy and algae), non-mammalian animal (such as for example krill, fish (such as for example Herring and blue Whiting), or microorganism (such as for example bacteria) source or any combinations thereof. In yet a further embodiment, the production of the lipid preparation involves an enzymatic catalysis.

In a further one of its aspects the present invention provides the preparations as herein disclosed for use in nutritional compositions, pharmaceutical compositions, nutraceutical compositions, parenteral nutrition composition, functional food or medical food.

In a further one of its aspects the present invention provides the preparations as herein disclosed for use in the preparation of nutritional compositions, pharmaceutical compositions, nutraceutical compositions, parenteral nutrition composition, functional food or medical food.

In another one of its aspects the present invention provides nutritional compositions, pharmaceutical compositions, nutraceutical compositions, parenteral nutrition compositions, functional food or medical food comprising a preparation according to the invention A nutritional composition as used herein may be any nutritional composition including, but not limited to: human milk fat substitute, parenteral formula composition, infant formula, adult formula, dairy product, milk powder, drinks, ice cream, biscuit, soy product, bakery, pastry, bread, cake, sauce, soup, prepared food, frozen food, condiment, confectionary, oil, fat, margarine, spread, filling, cereal, instant product, infant food, toddler food, bar, snack, candy, and chocolate product.

A functional food as used herein can be any functional food, including, but not limited to: dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy, and chocolate product.

A nutraceutical composition as used herein can be any nutraceutical, which can be any substance that may be considered as a food or part of a food and provides medical or health benefits, including the prevention and treatment of diseases or disorders. Such nutraceutical compositions include, but are not limited to: a food additive, a food supplement, a dietary supplement, genetically engineered foods (such as for example vegetables, herbal products, and processed foods such as cereals, soups, and beverages), stimulant functional food, medical food, parenteral nutrition, and pharma food. Dietary supplements may be delivered in the form of soft gel capsules, tablets, syrups, and other known dietary supplement delivery systems.

A medical food as used herein is specially formulated and intended for the dietary management of a disease/disorder that has distinctive nutritional needs that cannot be met by normal diet alone.

According to another embodiment, the pharmaceutical or nutraceutical compositions are in a dosage delivery form selected according to the route of administration.

The pharmaceutical, nutraceutical or medical food compositions may be in any of the many dosage delivery forms commonly used in the art. Pharmaceutical compositions suitable for oral administration may be presented as discrete dosage units (such as pills, tablets, pellets, dragees, capsules, sachet or softgel capsules), as a powder or granule, or as a liquid form, for example solution, suspension, syrup, or elixir. Solutions/suspensions may be formulated for intravenous administration.

Suitable routes of administration for the compositions of the subject invention are oral, nasal, intranasal, inhalation, buccal, sublingual administration, administration via a feeding tube, topical, transdermal, or parenteral (including subcutaneous, intramuscular, intravenous and intradermal) administration. In an embodiment, the compounds are administered orally.

The present invention also provides pharmaceutical compositions wherein a preparation according to the invention is admixed with (pharmaceutically) acceptable auxiliaries, and optionally other therapeutic agents. The auxiliaries must be "acceptable" in the sense of being compatible with the other ingredients of the composition and not deleterious to the recipients thereof.

In one embodiment of the present invention, a pharmaceutical composition of the present invention further comprises at least one additional pharmaceutically active agent.

For parenteral administration, suitable compositions include aqueous and non-aqueous sterile injection. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated.

The compositions may be presented in unit-dose or multi-dose containers, for example sealed vials and ampoules, and may be stored in a freeze-dried (lyophilized) condition requiring only the addition of sterile liquid carrier, for example water, prior to use.

According to another embodiment, the present invention can be administered in the form of capsules, tablets, pills, gummies, fluid oils, powders, granules, waxes, pastes, aqueous emulsions, and any other form that will enable its use in the target applications.

Compositions suitable for oral administration may be presented as discrete dosage units such as pills, tablets, pellets, dragees, capsules, powders, granules, solutions, suspensions, or elixirs.

The exact dose and regimen of administration of the composition will necessarily be dependent upon the therapeutic effect to be achieved and may vary with the particular formula, the route of administration, and the age and condition of the individual subject to whom the composition is to be administered.

The pharmaceutical and nutraceutical compositions of the present invention may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, desiccants, disintegrants, lubricants, colorants, flavoring agents, anti-oxidants, and wetting agents.

The pharmaceutical and nutraceutical compositions of the invention may further comprise edible fibers, aroma, taste ingredients, and ingredients that control physical and organoleptic properties.

According to another embodiment, a daily dose of the preparation of the invention as described herein optionally provides 1000 mg or less PS to the subject, at times 100-1000 mg PS, at times 100-600 mg PS, at times 100-500 mg PS, at times 100-400 mg PS, at times 100-300 mg PS, at times 2-600 mg PS, at times 2-500 mg PS, at times 2-300 mg PS, at times 2-200 mg PS, at times 4-150 mg PS, at times 4-100 mg PS, at times 6-100 mg PS, at times 8-100 mg PS, at times 10-90 mg PS, at times 10-80 mg PS, at times 10-40 mg PS and at times 20-40 mg PS. The daily dose may optionally be divided to a plurality of doses each day or alternatively may optionally be delivered as a single bolus each day.

The daily dose according to at least some embodiments of the present invention, when administrated as capsules, tablets, syrups, gummies, spray, syringe, dropper, tube' snorting (for powder), squeeze bottle delivery, atomized intranasal delivery (syringe or pump driven spraying devices), and other known delivery systems, optionally comprises one, two, three, four, five, six, seven or eight delivery units per day.

It should be noted that the preparation of the invention may also comprise other phospholipids, such as phosphatidylcholine (PC), phosphatidylethanolamine (PE), phosphatidylinositol (PI), and phosphatidylglycerol (PG), to which fatty acid acyls are covalently attached (bonded) at either or both of the sn-1 or sn-2 positions of the glycerol moiety of the phospholipid. The fatty acid conjugation profile of any of the above-noted polar lipids may be the same as, or different from, the fatty acid conjugation profile of PS, as disclosed herein.

In another one of its aspects the present invention provides nutritional compositions, pharmaceutical compositions, nutraceutical compositions, parenteral nutrition compositions, functional food or medical food comprising a preparation according to the invention for use in enteral or parenteral preparations for administration to a subject.

In another one of its aspects the present invention provides an infant formula, parenteral formula, baby food, toddler formula, child formula or adult formula comprising a preparation according to the invention for use in enteral or parenteral preparations for administration to a subject.

In another one of its aspects the present invention provides a method of promoting development in a subject, the method comprises administering to the subject a preparation according to the invention.

In another one of its aspects the present invention provides a preparation according to the invention for (or being used for, or being used in a method for) promoting development in a subject.

In another one of its aspects the present invention provides a method of preventing and/or treating development delay in a subject, the method comprises administering to the subject a preparation according to the invention.

In another one of its aspects the present invention provides a method of preventing and/or treating development delay in a preschooler child, the method comprises administering to the preschooler child a preparation according to the invention.

In another one of its aspects the present invention provides a preparation according to the invention for (or being used for, or being used in a method for) preventing and/or treating development delay in a subject.

In another one of its aspects the present invention provides a preparation according to the invention for (or being used for, or being used in a method for) preventing and/or treating development delay in a preschooler child.

In another one of its aspects the present invention provides a method of promoting brain and/or nervous system and/or cerebellar development in a subject, the method comprises administering to the subject a preparation according to the invention.

In another one of its aspects the present invention provides a preparation according to the invention for (or being used for, or being used in a method for) promoting brain and/or nervous system and/or cerebellar development in a subject.

In another one of its aspects the present invention provides a method of promoting white matter myelination and/or brain fiber organization in a subject, the method comprises administering to the subject a preparation according to the invention.

In another one of its aspects the present invention provides a preparation according to the invention for (or being used for, or being used in a method for) promoting white matter myelination and/or brain fiber organization in a subject.

In another one of its aspects the present invention provides a method of preventing and/or treating brain and/or nervous system and/or cerebellar development delay in a subject, the method comprises administering to the subject a preparation according to the invention.

In another one of its aspects the present invention provides a preparation according to the invention for (or being used for, or being used in a method for) preventing and/or treating brain and/or nervous system and/or cerebellar development delay in a subject.

In another one of its aspects the present invention provides a method of promoting cognitive development in a subject, the method comprises administering to the subject a preparation according to the invention.

In another one of its aspects the present invention provides a preparation according to the invention for (or being used for, or being used in a method for) promoting cognitive development in a subject.

In another one of its aspects the present invention provides a method of preventing and/or treating cognitive development delay in a subject, the method comprises administering to the subject a preparation according to the invention.

In another one of its aspects the present invention provides a preparation according to the invention for (or being used for, or being used in a method for) preventing and/or treating cognitive development delay in a subject.

In another one of its aspects the present invention provides a method of promoting visual and/or auditory development in a subject, the method comprises administering to the subject a preparation according to the invention.

In another one of its aspects the present invention provides a preparation according to the invention for (or being used for, or being used in a method for) promoting visual and/or auditory development in a subject.

In another one of its aspects the present invention provides a method of preventing and/or treating visual and/or auditory development delays in a subject, the method comprises administering to the subject a preparation according to the invention.

In another one of its aspects the present invention provides a preparation according to the invention for (or being used for, or being used in a method for) preventing and/or treating visual and/or auditory development delays in a subject.

In another one of its aspects the present invention provides a method of promoting language and speech development in a subject, the method comprises administering to the subject a preparation according to the invention.

In another one of its aspects the present invention provides a preparation according to the invention for (or being used for, or being used in a method for) promoting language and speech development in a subject.

In another one of its aspects the present invention provides a method of preventing and/or treating language and speech development delays in a subject, the method comprises administering to the subject a preparation according to the invention.

In another one of its aspects the present invention provides a preparation according to the invention for (or being used for, or being used in a method for) preventing and/or treating language and speech development delays in a subject.

In another one of its aspects the present invention provides a method of promoting social and/or emotional development in a subject, the method comprises administering to the subject a preparation according to the invention.

In another one of its aspects the present invention provides a preparation according to the invention for (or being used for, or being used in a method for) promoting social and/or emotional development in a subject.

In another one of its aspects the present invention provides a method of preventing and/or treating social and/or emotional development delays in a subject, the method comprises administering to the subject a preparation according to the invention.

In another one of its aspects the present invention provides a preparation according to the invention for (or being used for, or being used in a method for) preventing and/or treating social and/or emotional development delays in a subject.

In another one of its aspects the present invention provides a method of promoting motor development in a subject, the method comprises administering to the subject a preparation according to the invention.

In another one of its aspects the present invention provides a preparation according to the invention for (or being used for, or being used in a method for) promoting motor development in a subject.

In another one of its aspects the present invention provides a method of preventing and/or treating motor development delays in a subject, the method comprises administering to the subject a preparation according to the invention.

In another one of its aspects the present invention provides a preparation according to the invention for (or being used for, or being used in a method for) preventing and/or treating motor development delays in a subject.

In another one of its aspects the present invention provides a method of increasing brain weight in a subject, the method comprises administering to the subject a preparation according to the invention.

In another one of its aspects the present invention provides a preparation according to the invention for (or being used for, or being used in a method for) increasing brain weight in a subject.

In another one of its aspects the present invention provides a method of increasing the number and/or density of granule cells in a subject, the method comprises administering to the subject a preparation according to the invention.

In another one of its aspects the present invention provides a preparation according to the invention for (or being used for, or being used in a method for) increasing the number and/or density of granule cells in a subject.

In another one of its aspects the present invention provides a method for improving electrochemical synapse signaling in a subject, the method comprises administering to the subject a preparation according to the invention.

In another one of its aspects the present invention provides a preparation according to the invention for (or being used for, or being used in a method for) improving electrochemical synapse signaling in a subject.

In another one of its aspects the present invention provides a method for increasing neurogenesis in a subject, the method comprises administering to the subject a preparation according to the invention.

In another one of its aspects the present invention provides a preparation according to the invention for (or being used for, or being used in a method for) increasing neurogenesis in a subject.

In another one of its aspects the present invention provides a method for promoting fractional anisotropy (FA) of white matter in a subject, the method comprises administering to the subject a preparation according to the invention.

In another one of its aspects the present invention provides a preparation according to the invention for (or being used for, or being used in a method for) promoting fractional anisotropy (FA) of white matter in a subject.

In another one of its aspects the present invention provides a method for promoting neuroplasticity in a subject, the method comprises administering to the subject a preparation according to the invention.

In another one of its aspects the present invention provides a preparation according to the invention for (or being used for, or being used in a method for) promoting neuroplasticity in a subject. In another one of its aspects the present invention provides a method for improving membrane integrity in a subject, the method comprises administering to the subject a preparation according to the invention.

In another one of its aspects the present invention provides a preparation according to the invention for (or being used for, or being used in a method for) improving membrane integrity in a subject.

In another one of its aspects the present invention provides a method for increasing lipids uptake into cells, the method comprises administering to the subject a preparation according to the invention.

In another one of its aspects the present invention provides a preparation according to the invention for (or being used for, or being used in a method for) increasing lipids uptake into cells in a subject.

In another one of its aspects the present invention provides a method for reducing apoptosis rate, the method comprises administering to the subject a preparation according to the invention.

In another one of its aspects the present invention provides a preparation according to the invention for (or being used for, or being used in a method for) reducing apoptosis rate in a subject.

In another one of its aspects the present invention provides a method for increasing cells energy levels (e.g. ATP, carnitine levels) and/or cells protein levels, the method comprises administering to the subject a preparation according to the invention.

In another one of its aspects the present invention provides a preparation according to the invention for (or being used for, or being used in a method for) increasing cells energy levels (e.g. ATP, carnitine levels) and/or cells protein levels in a subject.

In another one of its aspects the present invention provides a method for increasing a secretase and/or Insulin-degrading enzyme activity and/or reducing $\beta$ and/or $\gamma$ secretase activity, the method comprises administering to the subject a preparation according to the invention.

In another one of its aspects the present invention provides a preparation according to the invention for (or being used for, or being used in a method for) increasing a secretase and/or Insulin-degrading enzyme activity and/or reducing $\beta$ and/or $\gamma$ secretase activity in a subject.

In another one of its aspects the present invention provides a method for promoting cell proliferation and/or enhancing cell viability in a subject, the method comprises administering to the subject a preparation according to the invention.

In another one of its aspects the present invention provides a preparation according to the invention for (or being used for, or being used in a method for) promoting cell proliferation and/or enhancing cell viability in a subject.

In another one of its aspects the present invention provides a method for increasing survival in a subject, the method comprises administering to the subject a preparation according to the invention.

In another one of its aspects the present invention provides a preparation according to the invention for (or being used for, or being used in a method for) increasing survival in a subject.

In another one of its aspects the present invention provides a method of promoting brain connectivity and/or brain maturation and/or functional responses of the brain and/or resting brain activity in a subject, the method comprises administering to the subject a preparation according to the invention.

In another one of its aspects the present invention provides a preparation according to the invention for (or being used for, or being used in a method for) promoting brain connectivity and/or brain maturation and/or functional responses of the brain and/or resting brain activity in a subject.

In another one of its aspects the present invention provides a method of promoting formation of cerebellar circuits in a subject, the method comprises administering to the subject a preparation according to the invention.

In another one of its aspects the present invention provides a preparation according to the invention for (or being used for, or being used in a method for) promoting formation of cerebellar circuits in a subject.

In another one of its aspects the present invention provides a method of promoting sensory and/or afferent nerve development in a subject, the method comprises administering to the subject a preparation according to the invention.

In another one of its aspects the present invention provides a preparation according to the invention for (or being used for, or being used in a method for) promoting sensory and/or afferent nerve development in a subject.

In another one of its aspects the present invention provides a method of promoting sensory and/or afferent nerve activity in a subject, the method comprises administering to the subject a preparation according to the invention.

In another one of its aspects the present invention provides a preparation according to the invention for (or being used for, or being used in a method for) promoting sensory and/or afferent nerve activity in a subject.

In another one of its aspects the present invention provides a method of promoting sensory processing and/or neural development in a subject, the method comprises administering to the subject a preparation according to the invention.

In another one of its aspects the present invention provides a preparation according to the invention for (or being used for, or being used in a method for) promoting sensory processing and/or neural development in a subject.

In another one of its aspects the present invention provides a method of promoting sensory event-related brain potentials in a subject, the method comprises administering to the subject a preparation according to the invention.

In another one of its aspects the present invention provides a preparation according to the invention for (or being used for, or being used in a method for) promoting sensory event-related brain potentials in a subject.

In another one of its aspects the present invention provides a method of promoting brain maturation and/or enhance inhibition of auditory related brain potentials (ERPs) in a subject, the method comprises administering to the subject a preparation according to the invention.

In another one of its aspects the present invention provides a preparation according to the invention for (or being used for, or being used in a method for) promoting brain maturation and enhance inhibition of auditory related brain potentials (ERPs) in a subject.

In another one of its aspects the present invention provides a method of promoting brain rehabilitation in a subject, the method comprises administering to the subject a preparation according to the invention. At times said subject underwent at least one of stroke, ischemic stroke, traumatic brain injury, seizures, epilepsy, concussion, intracerebral hemorrhage, cerebrovascular accident, developmental disorders, cerebral palsy.

In another one of its aspects the present invention provides a preparation according to the invention for (or being used for, or being used in a method for) promoting brain rehabilitation in a subject. At times said subject underwent at least one of stroke, ischemic stroke, traumatic brain injury, seizures, epilepsy, concussion, intracerebral hemorrhage, cerebrovascular accident, developmental disorders, cerebral palsy.

In another one of its aspects the present invention provides a method of preventing and/or treating brain injuries in a subject, the method comprises administering to the subject a preparation according to the invention. At times said subject underwent at least one of stroke, ischemic stroke, traumatic brain injury, seizures, epilepsy, concussion, intracerebral hemorrhage, cerebrovascular accident, developmental disorders, cerebral palsy.

In another one of its aspects the present invention provides a preparation according to the invention for (or being used for, or being used in a method for) preventing and/or treating brain injuries in a subject. At times said subject underwent at least one of stroke, ischemic stroke, traumatic brain injury, seizures, epilepsy, concussion, intracerebral hemorrhage, cerebrovascular accident, developmental disorders, cerebral palsy.

The term "infant formula" as used herein encompasses preterm formulas, premature formula, infant formulas (for newborn to 6 months old infants), follow-up formulas (for 6-12 months old babies), and growing up formulas (for 1-3 years old children).

As used herein, the term "subject" refers to a healthy subject or a subject suffering from a specific disorder (a non-healthy subject) or a subject at risk of developing a specific disorder. The subject may be a child including an infant, a toddler and a preschooler and an adult including a male, a female, a teenager, an elderly senior subject and a geriatric subject.

Optionally, in all aspects and embodiments of the present disclosure, the subject may be under parenteral nutrition or under partial parenteral nutrition.

Further, the term "child" includes infants (from day of birth, newborn, to about 12 months i.e., about 1 year) as well as toddlers (from about one year up to about the age of 3).

As used herein the term "preschooler child" refers to children from about 3 years old to about 5 years old.

An "infant" as used herein is meant to encompass a human infant, including but not limited to, a newborn, a very early preterm infant, a preterm infant, a premature infant, a term infant, a small for gestation infant and a small premature infants.

The term "newborn" includes pre-mature infants, post-mature infants and full term newborns.

The term "brain rehabilitation" as used herein refers to the process of brain recovery to as normal a condition as possible.

In some non-limiting embodiments the subject may suffer from one or more of reduced intestinal absorption, reduced gastrointestinal function, prematurity, intestinal inflammation, celiac disease, malabsorption related to different diseases, intestinal failure, short bowel syndrome, intestinal failure secondary to short bowel syndrome, congenital absorption defects, necrotizing enterocolitis, intestinal malformations, gastrointestinal fistulas, bowel obstruction, severe acute pancreatitis, cystic fibrosis, compromised intestinal function, Crohn's disease, cancer, a condition that result from low blood flow to the bowels, conditions which relate to and/or result from parenteral nutrition.

In some non-limiting embodiments the subject may suffer from one or more brain injuries which may result from one of the following examples: stroke, ischemic stroke, traumatic brain injury, seizures, epilepsy, concussion, intracerebral hemorrhage, cerebrovascular accident, developmental disorders, cerebral palsy. Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising," will be understood to imply the inclusion of a stated integer or step or group of integers or steps but not the exclusion of any other integer or step or group of integers or steps.

Example 1: The Effect of the Composition of the Invention on Cerebellar Development and Survival in a Pig Model Study Aim:

The effect of a composition according to the invention on cerebellar development was tested in a pig model of prematurely (preterm) delivered pigs (which corresponds to a development stage of about 32 week preterm infants). In addition, the effect of the composition on survival of preterm and term piglets was tested.

Methods:

Preterm pigs delivered from sows at 92% term (day 105 of 115 d of gestation) and term pigs were divided into 3 groups and supplemented with one of the following diets:
 a. Regular porcine milk replacer enriched with preparation A*
 b. Regular porcine milk replacer enriched with preparation B*
 c. Regular porcine milk replacer enriched with sunflower oil (which does not contain PS)

* For incorporation into milk replacer, preparation A and preparation B were mixed with sunflower oil in and 1:1.25 and 1:2 ratio, respectively.

Production of Preparation A: Marine lecithin extracted from biomass derived from fish was dissolved in organic solvents and allowed to react with an aqueous solution containing L-serine, CaCl2, phospholipase D (PLD) and acetate buffer. The resulting PS preparation was purified by removal of the water phase, evaporation of the organic solvents and further purification stages and contained 49.7% PS.

Production of Preparation B: PC enriched soybean lecithin was reacted with aqueous medium containing L-serine, CaCl2, PLD and acetate buffer. The resulting PS preparation was washed from water soluble material, further purified and then mixed in a 1:7.1 ratio with PS from marine lecithin (produced as described in "production of preparation A") and with maltodextrin to a final PS concentration of 32%.

The compositions of preparation A and B is described in Table 1.

TABLE 1

Tested preparations

|  | preparation A (according to the invention) | preparation B |
|---|---|---|
| PS % out of the preparation (w/w) | 50 | 32 |
| PS weight administrated per kg bodyweight per day (mg) | 48 | 48 |
| Linoleic acid (C18:2) attached to PS in the preparation with respect to the total fatty acid content attached to the PS in the preparation (%) | 0.7 | 8 |
| Docosahexaenoic acid (DHA) attached to PS in the preparation with respect to the total fatty acid content attached to the PS in the preparation (%) | 25 | 23 |
| % (w/w) of PS with carbon number of 34 carbons | >1% | Not detected |

Milk replacers were provided through the cheek into the distal esophagus via feeding tube every 3 h at 20 ml/kg.

During cultivation, pigs were monitored for survival rates.

After 10 days (for preterm piglets) and 0 or 20 days (for term piglets), pigs were euthanized and cerebella were removed, weighed and evaluated by immunohistochemistry. Each cerebellum was sectioned and sections were stained with an anti-Pax6 antibody, which specifically labels granule cells in the EGL. Confocal Z-stacks were generated and the number of granule cells per 200 μm of the EGL was determined in each cerebellum using unbiased stereological cell counts with Stereoinvestigator. Magnetic resonance imaging was performed to evaluate fractional anisotropy in white matter as well as fiber organization. MRI experiments were performed on a 7T/30 Bruker Biospec scanner. The piglet brains risen minimum of 48 hours with PBS, and placed on plastic bag filled with proton free solution, fluorinert solution (FC-770), prior to the MRI scanning.

In addition, development of auditory event-related brain potentials (ERPs) of pigs delivered 10 days preterm was evaluated. ERPs were recorded immediately after delivery and at days 2, 5, and 10 in response to pairs of 50-ms tones (500-ms inter-tone interval) that were presented during a 20-minute period with randomized inter-pair intervals (IPI) of 1 or 5 seconds. ERP morphology resembled that of humans, including clear N1 (negative peak approximately 100-ms post-stimulus) and P2 (positive peak approximately 200 ms post-stimulus) components.

Results:

Survival Rates

Survival rates of both preterm and term pigs were improved following feeding with milk replacer supplemented with preparation A (diet A) as compared to the control (diet C).

Survival rates following administration of preparation A are greater also in comparison with the survival rates following administration of preparation B.

Cerebella Weight:

Cerebellar weight was enhanced in piglets fed with milk replacer supplemented with preparation A as compared to piglets fed with the control milk replacer (diet C). This difference reached statistical significance (p=0.006). Interestingly, the cerebella weight of preterm piglets fed solely with milk replacer was significantly lower as compared to that of term piglets (p=0.03). In addition, only in preterm piglets fed with milk replacer supplemented with preparation A the cerebella weight at day 10 resulted in a non-significant difference (p>0.05) as compared to term piglets. It should be stated that term pigs in this experiment were pigs delivered vaginally and euthanized on day 0 post-delivery to serve as normal control for preterm pigs grown for 10 days.

Preparation A increases cerebellar weight of preterm piglets also in comparison with preparation B.

Number of Granule Cells

Figure 3:
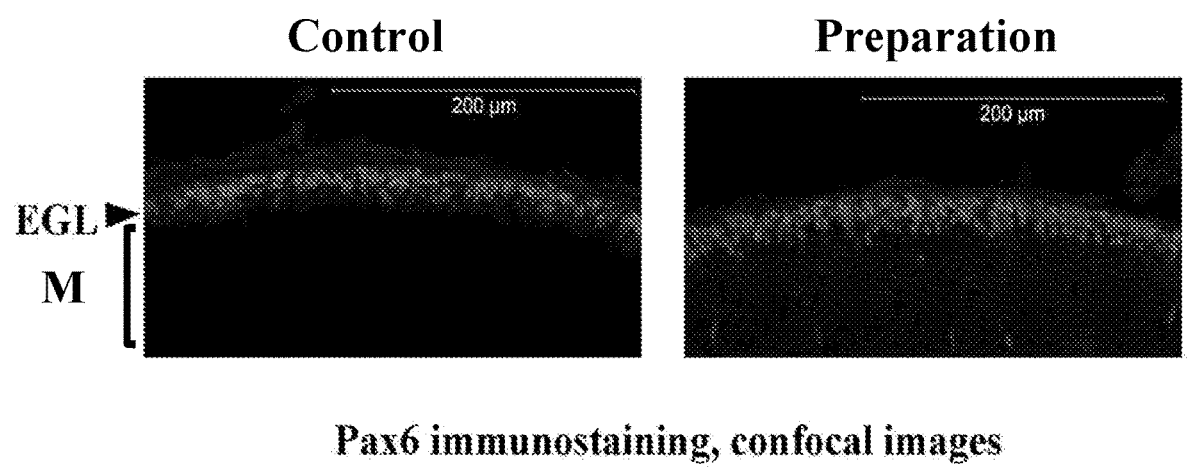
FIG. 3 are confocal images showing the external granule layer (EGL) and molecular layer (ML) of preterm piglets cerebellar following 10 days feeding with preparation A (diet A) or control diet (Diet C).
Figure 4:
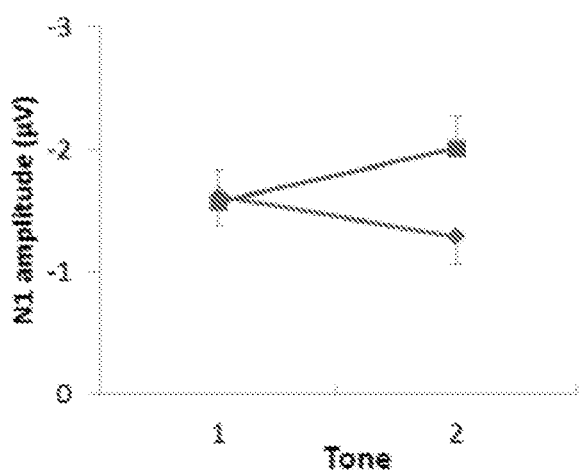
FIG. 4 shows the recorded results of auditory event-related brain potentials (ERPs). (Tone×Diet interaction, $F(1, 17)=5.075$, $p=0.038$, partial $\eta 2=0.230$)

As demonstrated in Table 2 and FIG. 3 the number of granule cells in external granule layer and in the molecular layer was increased in preterm piglets fed milk replacer supplemented with preparation A (diet A) as compared to piglets which received the control milk replacer (diet C).

Number of granule cells in external granule layer and in the molecular layer are increased in preterm piglets fed milk replacer supplemented with preparation A (diet A) as compared to piglets which received diet B.

TABLE 2

Number of granule cells at day 10

|  | Preparation A (n = 10) | Control-Diet C (n = 7) | P Value |
|---|---|---|---|
| number of granule cells per 200 μm of external granule layer Anti-Pax6 cell count ± SD | 181.03 ± 25.75 | 119.67 ± 29.40 | 0.000806 |

ERPs Results

N1: most negative peak 50-150 ms after tone-pair onset

P2: most positive peak 150-250 ms after tone-pair onset

Across days, the N1 peak amplitude for the second tone was larger for the control group compared with piglets supplemented with preparation A. This suggests that preparation A may have produced enhanced inhibition of the second tone—suggestive of enhanced maturation. N1 peak amplitude following administration of preparation A are lower also in comparison with N1 peak amplitude following administration of preparation B F represents the degree of freedomF(df1, df2)

P is p. value

η2n is eta$^2$ which relates to effect size

MRI Results

Figure 5:
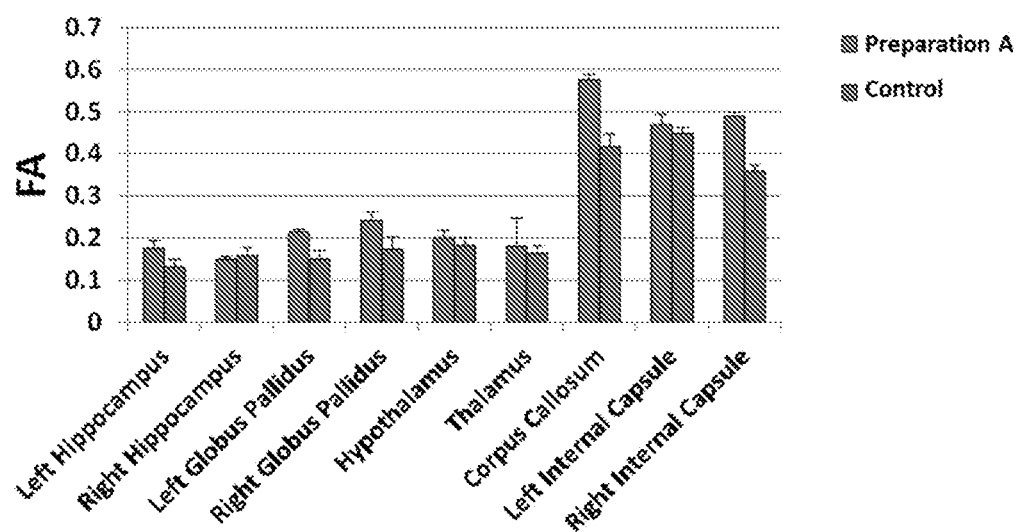
FIG. 5 illustrates functional anisotropy values of white matter in preterm piglets fed milk replacer supplemented with preparation A (diet A) as compared to piglets which received the control milk replacer (diet C).

As demonstrated in FIG. 5 functional anisotropy values of white matter increased in preterm piglets fed milk replacer supplemented with preparation A (diet A) as compared to piglets which received the control milk replacer (diet C). This suggests an enhanced white matter myelination and fiber organization in pigs fed milk replacement supplemented with preparation A.

Fractional anisotropy values following administration of preparation A are greater also in comparison with Fractional anisotropy values following administration of preparation B Conclusion According to the study results, Preparation A (in accordance with the invention) is superior to both preparation B and Diet C in improving survival of preterm and term piglets and in improving parameters related to brain structural and functional development of preterm piglets.

Example 2: The Effect of the Composition of the Invention on Cell's Structure and Function in a Neuronal Cell Culture Model Study Aim:

The effect of a composition according to the invention on neuronal cell structure and function was tested in a neuronal cell culture model.

Methods:

Neuronal cell cultures are incubated with one of the following preparations:

Preparation A: Marine lecithin extracted from biomass derived from fish was dissolved in organic solvents and allowed to react with an aqueous solution containing L-serine, CaCl2, phospholipase D (PLD) and acetate buffer. The resulting PS preparation was purified by removal of the water phase, evaporation of the organic solvents and further purification stages and contained 63% PS.

Preparation B: PC enriched soybean lecithin was reacted with aqueous medium containing L-serine, CaCl2, PLD and acetate buffer. The resulting PS preparation was washed from water soluble material, further purified and then mixed in a 1:1.5 ratio with PS from marine lecithin (produced as described in "production of preparation A") to a final PS concentration of 63%. The preparations were further treated with a mixture of EDTA-Na and solvents.

Compositions of preparation A and B are described in Table 3.

TABLE 3

Tested preparations

| | Preparation A (according to the invention) | Preparation B |
|---|---|---|
| PS % out of the preparation (w/w) | 63 | 63 |
| Linoleic acid (C18:2) attached to PS in the preparation with respect to the total fatty acid content attached to the PS in the preparation (%) | 0.17 | 26 |
| Docosahexaenoic acid (DHA) attached to PS in the preparation with respect to the total fatty acid content attached to the PS in the preparation (%) | 38 | 23 |

Cells are incubated with either preparation A or B and evaluated for membrane integrity, uptake of lipid compositions into cells, cell proliferation, total protein content, morphological changes and apoptosis. In addition, cells are evaluated for α, β and γ secretases as well as IDE activity, gene expression profile and energy levels (ATP and carnitine).

Results:

Membrane Integrity

Membrane integrity of cells incubated with preparation A is improved as compared to cells incubated with preparation B.

Uptake of Lipid Compositions into Cells

Uptake of lipid compositions into cells is higher using preparation A as compared to preparation B. Percentage of lipid integrated into the membrane is analyzed using lipidomics analyses.

Cell Proliferation

Cell proliferation is higher in cells treated with preparation A as compared to cells treated with Preparation B.

Total Protein Content

Total protein content is higher in cells treated with preparation A as compared to cells treated with Preparation B.

Apoptosis

Apoptosis is lower in cells treated with preparation A as compared to cells treated with Preparation B.

α, β and γ Secretases Activity

Cells treated with preparation A exhibit higher activity of a secretase as compared to cells treated with Preparation B. In addition, cells treated with preparation A exhibit lower activity of β and γ secretases as compared to cells treated with preparation B. Cells treated with preparation A also exhibit higher (Insulin-degrading enzyme) IDE activity as compared to cells treated with Preparation B.

Gene Expression

Gene expression analyses of cells treated with preparation B exhibit higher transcription of ADAM10, IDE and PSD95 as well as lower transcription of Nicastrin and BACE1 genes as compared to cells treated with Preparation B.

Energy Levels

Energy levels (expressed as ATP and carnitine levels) are higher in cells treated with preparation A as compared to cells treated with Preparation B.

Conclusion

According to the study results, Preparation A (in accordance with the invention) is superior to preparation B in improving membrane integrity, uptake of lipid compositions into cells, cell proliferation, total protein content, morphological changes and apoptosis as well as for enhancing activity of a secretase and IDE activity, reducing β and γ secretase activity. In addition, preparation B is superior to both preparation A and C in enhancing transcription of ADAM10, IDE and PSD while reducing transcription of Nicastrin and BACE1. Preparation B is also superior to A and C in elevating energy levels (ATP and carnitine).

The invention claimed is:

1. A preparation comprising a non-mammalian derived mixture of phosphatidylserine comprising a concentration of phosphatidylserine of at least 40% w/w, wherein the percentage of linoleic acid (C18:2) attached to PS in the preparation with respect to the total fatty acid content attached to the PS in the preparation is lower than 8%, the percentage of Docosahexaenoic acid (DHA) attached to PS in the preparation with respect to the total fatty acid content attached to the PS in the preparation is greater than 25%; and at least 1% (w/w) of the PS in the preparation have a carbon number of 34 carbons.

2. The preparation according to claim 1 wherein the percentage of linoleic acid (C18:2) attached to PS in the preparation with respect to the total fatty acid content attached to the PS in the preparation is lower than 2.5%.

3. The preparation according to claim 1 wherein the percentage of linoleic acid (C18:2) attached to PS in the preparation with respect to the total fatty acid content attached to the PS in the preparation is greater than 0.5%.

4. The preparation according to claim 1 wherein the at least 1% (w/w) of the PS in the preparation having carbon number of 34 carbons, have a double bond number of 1.

5. The preparation of claim 1 wherein the percentage of Docosahexaenoic acid (DHA) attached to PS in the preparation with respect to the total fatty acid content attached to the PS in the preparation is greater than 24% 28%.

6. The preparation of claim 1 wherein the preparation comprises at least 1% (w/w) PS with fatty acid composition of 40 carbons.

7. The preparation of according to claim 6 wherein the at least 1% (w/w) at of the PS in the preparation having a carbon number of 40 carbons, have a double bond number of 7.

8. The preparation according to claim 1 wherein the phosphatidylserine constitutes at least 50% w/w of the preparation.

9. A nutritional composition, pharmaceutical composition, nutraceutical composition, parenteral nutrition composition, functional food or medical food comprising the preparation according to claim 1 for use in enteral or parenteral preparations for administration to a subject.

10. An infant formula, parenteral formula, baby food, toddler formula, child formula or adult formula comprising the preparation according to claim 1 for use in enteral or parenteral preparations for administration to a subject.

11. A pharmaceutical or nutritional composition, comprising a non-mammalian derived mixture of phosphatidylserine (PS), wherein the percentage of linoleic acid (C18:2) attached to PS in the preparation with respect to the total fatty acid content attached to the PS in the preparation is 0.7%, wherein the percentage of Docosahexaenoic acid (DHA) attached to PS in the preparation with respect to the total fatty acid content attached to the PS in the preparation is 25%, wherein at least 1% (w/w) of the PS in the preparation have a carbon number of 34 carbons, further comprising one or more pharmaceutically or nutritionally acceptable excipients or carriers.

* * * * *